United States Patent [19]

Shibata et al.

[11] Patent Number: 5,723,621

[45] Date of Patent: Mar. 3, 1998

[54] PROCESS FOR PROCESSING BIARYL COMPOUND

[75] Inventors: Koichi Shibata; Shuichi Matsui; Kazutoshi Miyazawa, all of Chiba, Japan

[73] Assignee: Chisso Corporation, Osaka, Japan

[21] Appl. No.: 645,561

[22] Filed: May 14, 1996

[30] Foreign Application Priority Data

May 15, 1995 [JP] Japan .................................... 7-141117
Aug. 4, 1995 [JP] Japan .................................... 7-219592

[51] Int. Cl.$^6$ .......................... C07B 37/04; C07D 213/16
[52] U.S. Cl. .......................... 546/339; 544/180; 544/242;
544/336; 544/348; 549/29; 549/505; 558/411;
560/102; 568/325; 568/642; 570/123
[58] Field of Search ................... 546/348, 1, 349,
546/29, 505; 556/466; 544/180, 336, 242;
549/29, 505; 558/411; 560/102; 568/325,
642; 570/123

[56] References Cited

FOREIGN PATENT DOCUMENTS 03058942  3/1991  Japan .

OTHER PUBLICATIONS

"Highly Selective Cross–Coupling Reactions of Aryl (halo) silanes with Aryl Halides: A General and Pratical Route to Functionalized Biaryls", Hatanaka et al., *Tetrahedron*, 50, No. 28, pp. 8301–8316, 1994.
*Chemical Abstracts*, vol. 115, No. 15, 14 Oct. 1991, Columbus, Ohio, US; abstract No. 158687, T. Hiyama et al: "Preparation of biaryl compounds from arylisilanes", p. 892; column 1; XP002008958.

*Primary Examiner*—C. Warren Ivy
*Assistant Examiner*—Lyman H. Smith
*Attorney, Agent, or Firm*—Leydig, Voit & Mayer, Ltd.

[57] ABSTRACT

A novel process for producing a biaryl compound represented by formula (III), which is useful as a medicine, an agricultural chemical and an electrooptical liquid-crystal display material:

$$Ar\text{---}Ar' \qquad (III)$$

(wherein Ar and Ar' each independently represents a substituted or unsubstituted aromatic group) which comprises the steps of (i) reacting a trialkoxysilyl-substituted aromatic compound represented by formula (I):

$$Ar\text{---}Si(OR)_3 \qquad (I)$$

(wherein Ar has the same meaning as defined above and R represents an alkyl group having from 1 to 5 carbon atoms) with a fluoride ion source in the presence of a solvent, and then (ii) adding thereto an aromatic compound represented by formula (II):

$$X\text{---}Ar' \qquad (II)$$

(wherein X represents an eliminating group and Ar' has the same meaning as defined above) and a catalyst comprising a transition metal of tenth group to conduct a further reaction.

22 Claims, No Drawings

PROCESS FOR PROCESSING BIARYL COMPOUND

FIELD OF THE INVENTION

The present invention relates to a novel process for producing a biaryl compound useful as a medicine, an agricultural chemical and an electrooptical liquid-crystal display material.

BACKGROUND OF THE INVENTION

Liquid-crystal display modes most frequently used at present are TN (twisted nematic), STN (super-twisted nematic) and TFT (thin-film transistor) modes. Many of the liquid-crystalline compounds used in these modes have a biaryl skeleton. For attaining a lowered driving voltage or improved responsiveness, it is necessary to introduce a polar substituent such as a halogen atom, a cyano group or an alkoxy group into the skeleton of those compounds as described in <Kikan Kagaku Sōsetsu (the Elements of Chemistry, Quarterly Publication) No. 22> "Ekishō No Kagaku (Chemistry of Liquid Crystal)," edited by Chemical Society of Japan, Gakkai Shuppan Center (1994).

Various compounds having a biaryl skeleton are produced for use as synthetic medicines and agricultural chemicals. Many physiologically active natural products having such a skeleton also exist, as described in "Iyaku-hin No Kaihatsu (Development of Medicines)," Vols. 1–4, Hirokawa Shoten (1989); "Saishin Nōyaku Deita Bukku (Data Book on Latest Agricultural Chemicals)," Soft Science Sha (1982).

Most of the conventional processes for producing biaryl compounds are roughly divided into the following two groups.

(1) A process in which an available compound having a biaryl skeleton is used as a starting material and appropriate substituents are successively introduced into the rings or side chains thereof, as described in "Ekishō Kiso-hen (Liquid Crystal, Elementary Volume)," Baifukan, p. 234 (1985).

(2) A process in which a biaryl skeleton is formed by the cross-coupling reaction of aryl groups. Examples of this process include:

(2-1) The Gomberg-Bachmann-Hey reaction, in which a diazonium salt is reacted with an aromatic compound in the presence of a base, as described in J. Am. Chem. Soc., 46, 2339 (1924);

(2-2) The Pshorr reaction, in which an aromatic diazonium salt is coupled using a copper salt as a catalyst, as described in Ber. Dtsch. Ger., 29, 496 (1896);

(2-3) The Ullmann reaction, in which an aryl halide is heated together with a copper powder, as described in Ber., 34, 2174 (1901);

(2-4) A method in which an aromatic magnesium, zinc, tin, or boron compound is coupled with an aromatic halide in the presence of a transition metal compound as a catalyst, as described in "Kikan Kagaku Sōsetsu (the Elements of Chemistry, Quarterly Publication) No. 22, Ekishō No Kagaku (Chemistry of Liquid Crystal)," edited by Chemical Society of Japan, Gakkai Shuppan Center (1994), pp. 51–56; J. Organomet. Chem., 118, 349 (1976); J. Chem. Soc., Chem. Commun., 511 (1984); Tetrahedron Lett., 22, 5319 (1981); Tetrahedron, 42, 2111 (1986); J. Org. Chem., 42, 1821 (1977); J. Organomet. Chem., 250, 551 (1983); Tetrahedron Lett., 28, 5093 (1987); and Synth. Commun., 11, 513 (1981)); and (2-5) A method in which a halosilyl-substituted aromatic compound is reacted with an aromatic halide in the presence of a palladium catalyst, as described in JP-A-3-58942 (The term "JP-A" as used herein means an "unexamined published Japanese patent application."), JP-A-6-239770, JP-A-6-239766 and J. Synth. Org. Chem. Jpn., 48, 834 (1990).

However, these prior art methods do not provide results satisfying any or some of various requirements required for the preparation of biaryl compounds.

Process (1), in which an available compound having a biaryl skeleton is used as a starting material and substituents are introduced into side chains or the rings thereof, is disadvantageous in that the kinds of available compounds having a biaryl skeleton are limited, and that it is exceedingly difficult to introduce a fluorine atom and other substituents in specific positions. Moreover, terminal groups should be successively introduced, so that the number of all steps necessary for obtaining the objective compound from the starting material is very large. A further disadvantage is that a compound having a central skeleton comprising three or more rings is difficult to produce according to this process on an industrial scale, because of the necessity of an increased number of steps and the reduced solubility of the intermediate thereof.

The number of steps in Process (2) for forming a desired biaryl skeleton can be reduced by selecting aromatic compounds having appropriate substituents. However, the reactions shown in (2-1) to (2-5) have many problems as follows.

Among those methods, methods (2-1), (2-2) and (2-3) are disadvantageous in that compounds having a hydroxyl, amino, cyano or another group are less apt to undergo the expected reaction. Furthermore, such compounds often give a homocoupling reaction product as the main reaction product to make it difficult to selectively obtain a cross-coupling reaction product. Namely, the yield of the objective compound is low.

Method (2-4) has an advantage that a cross-coupling reaction product can be selectively obtained. However, also in this method, compounds having a hydroxyl, amino, cyano, carbonyl or another group are less apt to undergo the expected reaction.

Method (2-5) can be applied to biaryl compounds having substituents selected from various groups as described above. However, when this method is applied to produce a biaryl compound having a cyano group, the yield of the product falls below 80%. Thus, an objective biaryl compound cannot necessarily obtained in satisfactory yield according to this method. Further disadvantages are that N,N-dimethyl-formamide (DMF), which is expensive, should be used as a solvent for the reaction, that the reaction system is heterogeneous, and that because halosilane derivatives are susceptible to hydrolysis, reagent instability is expected and sufficient care should be taken in reagent handling. These disadvantages are serious obstacles to industrial application of the method.

As described above, known methods have many problems including the necessity of a larger number of steps and a low yield of the objective compound. In other words, known methods are unsuitable for the mass production of a biaryl compound having specific substituents in specific positions through a small number of steps in a good yield. Particularly in Method (2-5), halosilane derivatives which are key compounds of this reaction are not stable because of their susceptibility to hydrolysis as described above. Therefore, sufficient care should be taken in handling.

SUMMARY OF THE INVENTION

An object of the present invention is to provide a novel and efficient process for producing a compound having a biaryl skeleton, in particular, a biaryl compound having a cyano, carbonyl or hydroxyl group on the aromatic rings or a polyfunctional polycyclic compound comprising three or more rings; the production of such compounds have had problems as described above.

As a result of investigations made by the present inventors on simple processes for producing a biaryl compound which may have at least one functional group, it has been found that a cross-coupling reaction product can be obtained in a good yield by reacting a trialkoxysilyl-substituted aromatic compound with an aromatic compound having an eliminating group in the presence of a catalyst comprising a transition metal of tenth group and a fluoride ion source. The present invention has been completed based on this finding.

The present invention provides, in one embodiment thereof, a process for producing a biaryl compound represented by formula (III):

Ar—Ar'  (III)

(wherein Ar and Ar' each independently represents a substituted or unsubstituted aromatic group) which comprises the steps of:

(i) reacting a trialkoxysilyl-substituted aromatic compound represented by formula (I):

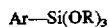
Ar—Si(OR)₃  (I)

(wherein Ar has the same meaning as defined above and R represents an alkyl group having from 1 to 5 carbon atoms) with a fluoride ion source in the presence of a solvent; and then (ii) adding thereto an aromatic compound represented by formula (II):

X—Ar'  (II)

(wherein X represents an eliminating group and Ar' has the same meaning as defined above) and a catalyst comprising a transition metal of tenth group to conduct a further reaction.

The present invention further provides, in another embodiment thereof, a process for producing a biaryl compound represented by formula (III):

Ar—Ar'  (III)

(wherein Ar and Ar' each independently represents a substituted or unsubstituted aromatic group) which comprises the steps of:

(i) adding a fluoride ion source to a mixture of a trialkoxysilyl-substituted aromatic compound represented by formula (I):

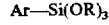
Ar—Si(OR)₃  (I)

(wherein Ar has the same meaning as defined above and R represents an alkyl group having from 1 to 5 carbon atoms) and an aromatic compound represented by formula (II):

X—Ar'  (II)

(wherein X represents an eliminating group and Ar' has the same meaning as defined above) in the presence of a solvent to react the reactants; and then (ii) adding thereto a catalyst comprising a transition metal of tenth group to conduct a further reaction.

DETAILED DESCRIPTION OF THE INVENTION

Examples of the aromatic groups in the compounds respectively represented by formulae (I) and (II) include a phenyl group, a biphenyl group, a naphthyl group, a pyridyl group, a pyrimidyl group, a pyrazyl group, a furyl group, a thienyl group and a triazyl group.

Examples of the substituent with which the aromatic group of the trialkoxysilyl-substituted aromatic compound represented by formula (I) may be substituted include hydrocarbon groups having from 1 to 17 carbon atoms, alkoxy groups having from 1 to 10 carbon atoms, alkoxyalkyl groups having from 2 to 10 carbon atoms (the hydrocarbon group in each of these substituents may be linear, branched or cyclic, may be saturated or unsaturated, and may be wholly or partly substituted with fluorine atoms), a fluorine atom, and a hydrogen atom. Of these, saturated linear hydrocarbon groups having from 1 to 7 carbon atoms, substituted groups thereof obtained by replacing a methylene group thereof with an oxygen atom, trans-4-alkylcyclohexyl groups (in which the alkyl group is selected from the above saturated linear hydrocarbon groups and the substituted groups thereof) and a fluorine atom are preferred. Two or more substituents may be present on the aromatic group.

Examples of the alkoxy groups in the trialkoxysilyl group include a methoxy group, an ethoxy group, a propoxy group, a butoxy group and a pentyloxy group. Of these, a methoxy group and an ethoxy group are preferred. Further, a methoxy group is more preferred, because it is sterically small.

Examples of the substituent with which the aromatic group of the aromatic compound represented by formula (II) may be substituted include hydrocarbon groups having from 1 to 17 carbon atoms, alkoxy groups having from 1 to 10 carbon atoms, acyl groups having from 2 to 10 carbon atoms, alkoxycarbonyl groups having from 2 to 10 carbon atoms, alkoxycarbonylalkyl groups having from 3 to 10 carbon atoms, hydroxyalkyl groups having from 2 to 7 carbon atoms, alkoxyalkyl groups having from 2 to 7 carbon atoms (the hydrocarbon group in each of these substituents may be linear, branched or cyclic, may be saturated or unsaturated, and may be wholly or partly substituted with fluorine atoms), a hydroxyl group, a formyl group, a cyano group, a nitro group, a fluorine atom, a chlorine atom and a hydrogen atom. Of these, saturated linear hydrocarbon groups having from 1 to 7 carbon atoms, substituted groups thereof obtained by replacing a methylene group thereof with an oxygen atom, trans-4-alkylcyclohexyl groups (in which the alkyl group is selected from the above saturated linear hydrocarbon groups and the substituted groups thereof), acyl groups having from 2 to 7 carbon atoms and a fluorine atom are preferred. Two or more substituents may be present on the aromatic group.

Examples of the eliminating group X include a bromine atom, an iodine atom, a p-toluenesulfonyloxy group, a methanesulfonyloxy group and a trifluoromethanesulfonyloxy group.

Compounds represented by formula (III) which have various substituents such as those enumerated above are exceedingly important compounds for use as liquid-crystalline compounds or intermediates therefor. For example, compounds represented by formula (III) having a cyano substituent are frequently used as liquid-crystalline compounds, while compounds represented by formula (III) having a formyl substituent can be easily converted to esters useful as liquid-crystalline compounds after the formyl group is converted to a carboxyl group.

A substituted or unsubstituted benzene and a substituted or unsubstituted pyridine, pyrimidine, pyrazine, furan, thiophene or triazine are converted into compounds respectively represented by formulae (I) and (II) (in some cases (II) and (I)) and then subjected to cross-coupling reaction, whereby a medicine, an agricultural chemical, or an intermediate therefor can be obtained.

Trialkoxysilyl-substituted aromatic compounds represented by formula (I) can be produced according to the following two methods (A) and (B), which are described in J. Org. Chem., 55, 2415 (1990). Some of those compounds are commercially available.

(A) A method in which one of various Grignard reagents is reacted with a tetraalkoxysilane.

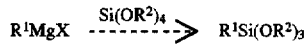

(B) A method in which one of various Grignard reagents is reacted with tetrachlorosilane, and the reaction product is treated with an alcohol.

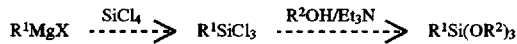

In methods (A) and (B) in the above-cited reference, $R^1$ is a hydrocarbon group represented by an allyl group and $R^2$ is a methyl group. The trialkoxysilyl-substituted aromatic compound represented by formula (I) can be prepared by employing an aryl group as $R^1$, and an alkyl group as $R^2$ in the above method (A) or (B).

Since the compounds represented by formula (I) are stable to moisture and heat, they can be easily handled and stored for a long period of time.

Examples of the fluoride ion source introduced into the reaction system include fluoride salts of either alkali metals or alkaline earth metals (e.g., potassium fluoride and magnesium fluoride), quaternary ammonium salts (e.g., tris (diethylamino)sulfonium difluorotrimethylsilicate (TASF) and tetrabutylammonium fluoride (TBAF). Especially preferred is TBAF. The fluoride ion source is used in an amount of preferably at least 1.0 mol, particularly preferably from 1.0 to 1.1 mol, per mol of the compound represented by formula (I).

The catalyst comprising a transition metal of tenth group for use in the present invention may be a complex having a phosphine ligand, or a salt having no phosphine ligand.

Examples of the catalyst comprising a transition metal of tenth group for use in the reaction include nickel compounds (e.g., tetrakis(triphenylphosphine)nickel(0) and nickel(II) chloride) and platinum compounds (e.g., bis (dibenzalacetone)platinum(0) and tetrakis (triphenylphosphine)platinum(0)). However, preferable catalysts are palladium salts and palladium complexes. Examples of usable palladium catalysts include di-μ-chlorobis(allyl)dipalladium(II), allyl(cyclopentadienyl) palladium(II), dichloro(tetraphenylcyclobutadiene) palladium(II), di-μ-chloro-dichlorobis(ethylene)dipalladium (II), dichlorobis(triphenylphosphine)palladium(II), palladium(II) acetate, palladium(II) chloride, tetrakis (triphenylphosphine)palladium(0), bis[1,2-bis (diphenylphosphino)ethane]palladium(0), bis[1,3-bis (diphenylphosphino)propane]palladium(0), bis[1,4-bis (diphenylphosphino)butane]palladium(0) and [1,1'-bis (diphenylphosphino)ferrocene]palladium(II) chloride. Along with these catalysts, a catalytic amount of at least one phosphine ligand or at least one phosphorous triester may be used for the reaction. An especially preferred catalyst is tetrakis(triphenylphosphine)palladium(0). The catalyst may be used in an amount of from 0.01 to 20 mol % based on the molar amount of the aromatic compound. In order for the reaction to proceed satisfactorily, the catalyst amount is preferably from 0.1 to 10 mol %, particularly preferably from 1 to 7 mol %.

The solvent for use in the reaction of the present invention can be suitably selected, according to the compound to be produced, from a variety of solvents ranging from nonpolar hydrocarbon solvents to polar solvents such as ethers and amides. These solvents may be used alone or as a mixture of two or more thereof. Toluene alone or a toluene/ tetrahydrofuran (THF) mixed solvent is especially preferably used to conduct the reaction therein.

The reaction is preferably conducted in a solvent at a temperature of from room temperature (20° C.) to 200° C. Although there is a wide choice of the reaction temperature, a moderately high temperature is preferred because the rate of reaction at around room temperature is very low. The optimum temperature range is from 60° to 110° C.

Compounds represented by formula (III) can be thus produced. Representative examples of these compounds obtained by the process of the present invention, along with the yields and phase transition temperatures thereof, are shown in Tables 1 to 3 given in Examples.

The present invention will be described below in more detail by reference to Examples thereof, but the invention should not be construed as being limited thereto.

(1) The phenyltrimethoxysilane (compound (Ia) in Table 1) used for the reaction was commercial available. The other aryltrimethoxysilanes (I) shown in Tables 1 to 3 were prepared as follows.

Preparation of 4-(4-propylcyclohexyl) phenyltrimethoxysilane (compound (Ih) in Table 2):

A THF (600 ml) solution of 5.35 g (200 mmol) of magnesium and 56.2 g (220 mmol) of 4-(4-propylcyclohexyl)-bromobenzene was stirred at 50° C. for 2.5 hours under nitrogen.

To a THF (108 ml) solution of 32.4 ml (220 mmol) of tetramethoxysilane was added dropwise the Grignard reagent prepared above at 0° C. over a period of 2 hours and stirred for 17 hours while being gradually heated to room temperature. After the solvent had been evaporated under reduced pressure, 500 ml of heptane and 300 ml of saturated aqueous ammonium chloride solution were added to the residue and filtered through a Celite. The organic layer was separated and the aqueous layer was extracted with heptane three times. The combined organic layer was dried over magnesium sulfate. After the magnesium sulfate was removed by filtration, the filtrate was evaporated under reduced pressure. The residue was distilled in vacuo to obtain 25.6 g (40%) of 4-(4-propylcyclohexyl) phenyltrimethoxysilane as a fraction at 170°–176° C./3 mmHg (1 mmHg=133.3 Pa).

Compounds Ib to Ig and Ii to II (see Tables 1 to 3) were prepared in a similar manner to that described above.

(2) Biaryl compounds represented by formula (III) shown in Tables 1 to 3 were prepared as follows.

Preparation of 4-(4-propylcyclohexyl)-3',4'-difluorobiphenyl (compound (IIIl) in Table 2):

To 0.645 g (2 mmol) of 4-(4-propylcyclohexyl)-phenyltrimethoxysilane (Ih) was added 2.1 ml of TBAF (2.1 mmol, 1M in THF) under nitrogen, and the mixture was stirred at room temperature for 30 minutes. After the solvent was removed under reduced pressure, a solution of 3,4-difluorobromobenzene (0.463 g, 2.4 mmol) in toluene (1 ml) was added, followed by the addition of a suspension of tetrakis(triphenylphosphine)palladium(0) (0.116 g, 0.1 mmol) in toluene (3 ml). The resulting mixture was refluxed for 3 hours. After cooling, to the reaction mixture were added water and toluene. The organic layer was separated and the aqueous layer was extracted with toluene three times. The combined organic layer was dried over magnesium sulfate. After the magnesium sulfate was removed by filtration, the filtrate was evaporated under reduced pressure. The residue was purified by silica gel column chromatography (heptane) to obtain 0.594 g (40%) of white crystals.

Compounds IIIa to IIIk and IIIm to IIIaf were prepared in a similar manner to that described above. The yields and phase transition temperatures of the products are also shown in Tables 1 to 3.

TABLE 1

| Entry | R—⌬—Si(OMe)₃ [I] | | Br—Ar [II] Ar | | [III] | | Yield (%) | Phase transition temperature (°C.) |
|---|---|---|---|---|---|---|---|---|
| | R | | | | | | | |
| 1 | H | [Ia] | –⌬–CH₂COOCH₂CH₂F | | ⌬–⌬–CH₂COOCH₂CH₂F | [IIIa] | 87 | C61I |
| 2 | $C_3H_7-$ | [Ib] | –⌬–CF₃ | | $C_3H_7$–⌬–⌬–CF₃ | [IIIb] | 93 | C40I |
| 3 | $C_5H_{11}-$ | [Ic] | –⌬–CN | | $C_5H_{11}$–⌬–⌬–CN | [IIIc] | 82 | C22N35I |
| 4 | " | [Ic] | –⌬(F,F) | | $C_5H_{11}$–⌬–⌬(F,F) | [IIId] | 45 | oily substance |
| 5 | " | [Ic] | –⌬(N) | | $C_5H_{11}$–⌬–⌬(N) | [IIIe] | 64 | oily substance |
| 6 | " | [Ic] | –⌬–COCH₃ | | $C_5H_{11}$–⌬–⌬–COCH₃ | [IIIf] | 38 | C88I |
| 7 | $CH_3O-$ | [Id] | –⌬(F) | | $CH_3O$–⌬–⌬(F,F) | [IIIg] | 53 | C39I |

TABLE 1-continued

| Entry | R—⟨benzene⟩—Si(OMe)₃ [I] R | [I] | Br—Ar [II] Ar | [III] | Yield (%) | Phase transition temperature (°C.) |
|---|---|---|---|---|---|---|
| 8 | C₄H₉O— | [Ie] | ⟨pyridine with C₄H₉⟩ | C₄H₉O—⟨⟩—⟨pyridine⟩—C₄H₉ [IIIh] | 81 | C48S88I |
| 9 | C₅H₁₁O— | [If] | O₂N—⟨⟩— | C₅H₁₁O—⟨⟩—⟨⟩—NO₂ [IIIi] | 80 | C55(N42)I |
| 10 | ⟨cyclohexyl-C₂H₅⟩ | [Ig] | F,F-⟨⟩— | C₂H₅—⟨cyclohexyl⟩—⟨⟩—⟨⟩-F,F [IIIj] | 88 | C69(N61)I |
| 11 | " | [Ig] | EtOOC—⟨⟩— | C₂H₅—⟨cyclohexyl⟩—⟨⟩—⟨⟩—COOC₂H₅ [IIIk] | 32 | S170I |

TABLE 2

| Entry | R | | Ar | [III] | | Yield (%) | Phase transition temperature (°C.) |
|---|---|---|---|---|---|---|---|
| 12 | C3H7-cyclohexyl | [Ih] | 3,4-difluorophenyl | C3H7-Cy-Ph-Ph(3,4-F2) | [IIIh] | 94 | C67N98I |
| 13 | " | [Ih] | 3-OCH3-phenyl | C3H7-Cy-Ph-Ph(3-OCH3) | [IIIm] | 66 | C53I |
| 14 | " | [Ih] | 2-OCH3-phenyl | C3H7-Cy-Ph-Ph(2-OCH3) | [IIIn] | 47 | C85I |
| 15 | " | [Ih] | 4-OCH3-phenyl | C3H7-Cy-Ph-Ph(4-OCH3) | [IIIo] | 50 | C108N204I |
| 16 | " | [Ih] | 4-F-phenyl | C3H7-Cy-Ph-Ph(4-F) | [IIIp] | 64 | C96N54I |
| 17 | " | [Ih] | 3,4,5-trifluorophenyl | C3H7-Cy-Ph-Ph(3,4,5-F3) | [IIIq] | 52 | C40(N35)I |
| 18 | " | [Ih] | 4-NO2-phenyl | C3H7-Cy-Ph-Ph(4-NO2) | [IIIr] | 46 | C119N187I |
| 19 | " | [Ih] | 4-CN-phenyl | C3H7-Cy-Ph-Ph(4-CN) | [IIIs] | 55 | C132N216I |
| 20 | " | [Ih] | 3-F,4-(4-C3H7-cyclohexyl)phenyl | C3H7-Cy-Ph-Ph(3-F,4-Cy-C3H7) | [IIIt] | 87 | C97I |
| 21 | C5H11-cyclohexyl | [Ii] | 3,4-difluorophenyl | C5H11-Cy-Ph-Ph(3,4-F2) | [IIIu] | 80 | C55N108I |
| 22 | " | [Ii] | 2-CN-phenyl | C5H11-Cy-Ph-Ph(2-CN) | [IIIv] | 39 | C80I |

TABLE 3

| Entry | R | | Ar | [III] | | Yield (%) | Phase transition temperature (°C.) |
|---|---|---|---|---|---|---|---|
| 23 | C5H11-cyclohexyl | [Ii] | 3-CN-phenyl | C5H11-Cy-Ph-Ph(3-CN) | [IIIw] | 32 | C69I |
| 24 | " | [Ii] | 4-CN-phenyl | C5H11-Cy-Ph-Ph(4-CN) | [IIIx] | 48 | C94N218I |

TABLE 3-continued

| Entry | R (in R—⟨⟩—Si(OMe)₃ [I]) | [II] Br—Ar / Ar | [III] | Yield (%) | Phase transition temperature (°C.) |
|---|---|---|---|---|---|
| 25 | " [Ii] | —⟨⟩—C₂H₅ | C₅H₁₁—⟨⟩—⟨⟩—⟨⟩—C₂H₅ | [IIIy] 95 | C34S146 N164I |
| 26 | " [Ii] | —⟨⟩—OCF₃ | C₅H₁₁—⟨⟩—⟨⟩—⟨⟩—OCF₃ | [IIIz] 91 | C43S128 N147I |
| 27 | " [Ii] | —⟨⟩—⟨⟩—C₃H₇ | C₅H₁₁—⟨⟩—⟨⟩—⟨⟩—C₃H₇ | [IIIaa] 95 | C90(S88) N291I |
| 28 | CH₃OCH₂—⟨⟩— [Ij] | —⟨⟩(F)—F | CH₂OCH₂—⟨⟩—⟨⟩—⟨⟩(F)—F | [IIIab] 41 | C98I |
| 29 | " [Ij] | —⟨⟩—NO₂ | CH₃OCH₂—⟨⟩—⟨⟩—⟨⟩—NO₂ | [IIIac] 53 | C172N179I |
| 30 | C₅H₁₁—⟨⟩— [Ik] | —⟨⟩—CN | C₅H₁₁—⟨⟩—⟨⟩—⟨⟩—CN | [IIad] 84 | C129N239I |
| 31 | C₃H₇—⟨⟩—⟨⟩— [Il] | —⟨⟩(F)—F | C₃H₇—⟨⟩—⟨⟩—⟨⟩(F)—F | [IIIac] 93 | C101N261I |
| 32 | " [Il] | —⟨⟩(F)(F)—F | C₃H₇—⟨⟩—⟨⟩—⟨⟩(F,F)—F | [IIIaf] 89 | S251N310I |

According to the process of the present invention, many biaryl compounds for use as liquid-crystalline materials, medicines, agricultural chemicals and intermediates therefor can be obtained through a reduced number of steps in good yields. The reaction using a halosilyl-substituted aromatic compound as described above under "Background of the Invention" is disadvantageous in that not only the reagent is susceptible to hydrolysis to have significantly reduced reactivity, but also the resulting hydrogen halide is harmful to the human body and may corrode the equipment. In contrast, the trialkoxysilyl-substituted aromatic compound used in the present invention is a stable compound free from the above described disadvantages, and can be easily handled. Therefore, the process of the present invention is industrially extremely useful.

While the invention has been described in detail and with reference to specific examples thereof, it will be apparent to one skilled in the art that various changes and modifications can be made therein without departing from the spirit and scope thereof.

What is claimed is:

1. A process for producing a biaryl compound represented by formula (III):

Ar—Ar'  (III)

(wherein Ar and Ar' each independently represents a substituted or unsubstituted aromatic group) which comprises the steps of:

(i) reacting a trialkoxysilyl-substituted aromatic compound represented by formula (I):

Ar—Si(OR)₃  (I)

(wherein Ar has the same meaning as defined above and R represents an alkyl group having from 1 to 5 carbon atoms) with a fluoride ion source in the presence of a solvent; and then (ii) adding thereto an aromatic compound represented by formula (II):

X—Ar'  (II)

(wherein X represents an eliminating group and Ar' has the same meaning as defined above) and a catalyst comprising a transition metal of tenth group to conduct a further reaction.

2. A process for producing a biaryl compound represented by formula (III):

Ar—Ar'  (III)

(wherein Ar and Ar' each independently represents a substituted or unsubstituted aromatic group) which comprises the steps of:

(i) adding a fluoride ion source to a mixture of a trialkoxysilyl-substituted aromatic compound represented by formula (I):

Ar—Si(OR)₃  (I)

(wherein Ar has the same meaning as defined above and R represents an alkyl group having from 1 to 5 carbon atoms) and an aromatic compound represented by formula (II):

X—Ar'  (II)

(wherein X represents an eliminating group and Ar' has the same meaning as defined above) in the presence of a solvent to react the reactants; and then (ii) adding thereto a catalyst comprising a transition metal of tenth group to conduct a further reaction.

3. The process for producing a biaryl compound as claimed in claim 1, wherein said catalyst is a complex having at least one phosphine ligand.

4. The process for producing a biaryl compound as claimed in claim 2, wherein said catalyst is a complex having at least one phosphine ligand.

5. The process for producing a biaryl compound as claimed in claim 1, wherein said catalyst is a salt having no phosphine ligand.

6. The process for producing a biaryl compound as claimed in claim 2, wherein said catalyst is a salt having no phosphine ligand.

7. The process for producing a biaryl compound as claimed in claim 1, wherein said catalyst has a phosphine ligand and is added together with either at least one phosphine ligand or at least one phosphorous triester.

8. The process for producing a biaryl compound as claimed in claim 2, wherein said catalyst has a phosphine ligand and is added together with either at least one phosphine ligand or at least one phosphorous triester.

9. The process for producing a biaryl compound as claimed in claim 1, wherein said catalyst has no phosphine ligand and is added together with either at least one phosphine ligand or at least one phosphorous triester.

10. The process for producing a biaryl compound as claimed in claim 2, wherein said catalyst has no phosphine ligand and is added together with either at least one phosphine ligand or at least one phosphorous triester.

11. The process for producing a biaryl compound as claimed in claim 1, wherein said trialkoxysilyl-substituted aromatic compound represented by formula (I) comprises a trimethoxysilyl-substituted aromatic compound.

12. The process for producing a biaryl compound as claimed in claim 2, wherein said trialkoxysilyl-substituted aromatic compound represented by formula (I) comprises a trimethoxysilyl-substituted aromatic compound.

13. The process for producing a biaryl compound as claimed in claim 1, wherein said fluoride ion source comprises tetrabutylammonium fluoride.

14. The process for producing a biaryl compound as claimed in claim 2, wherein said fluoride ion source comprises tetrabutylammonium fluoride.

15. The process for producing a biaryl compound as claimed in claim 1, wherein said catalyst is used in an amount of from 0.01 to 20 mol % based on the molar amount of the aromatic compounds.

16. The process for producing a biaryl compound as claimed in claim 2, wherein said catalyst is used in an amount of from 0.01 to 20 mol % based on the molar amount of the aromatic compounds.

17. The process for producing a biaryl compound as claimed in claim 1, wherein said solvent comprises toluene.

18. The process for producing a biaryl compound as claimed in claim 2, wherein said solvent comprises toluene.

19. The process for producing a biaryl compound as claimed in claim 1, wherein said solvent comprises a toluene/tetrahydrofuran mixed solvent.

20. The process for producing a biaryl compound as claimed in claim 2, wherein said solvent comprises a toluene/tetrahydrofuran mixed solvent.

21. The process for producing a biaryl compound as claimed in claim 1, wherein said process is conducted at from room temperature to 200° C.

22. The process for producing a biaryl compound as claimed in claim 2, wherein said process is conducted at from room temperature to 200° C.

* * * * *